United States Patent [19]

Frick et al.

[11] 4,213,990

[45] Jul. 22, 1980

[54] 1,1-DIPHENYLETHENE DERIVATIVES AS MICROBICIDES

[75] Inventors: Willy Frick, Pfeffingen; Adolf Hubele, Magden, both of Switzerland

[73] Assignee: Ciba-Geigy Corporation, Ardsley, N.Y.

[21] Appl. No.: 19,994

[22] Filed: Mar. 12, 1979

[30] Foreign Application Priority Data

Mar. 17, 1978 [CH] Switzerland ............... 2931/78

[51] Int. Cl.$^2$ ............... A01N 9/22; C07D 233/58; C07D 249/08
[52] U.S. Cl. ............... 424/269; 260/465 G; 260/649 F; 260/651 F; 548/341; 548/262; 424/245; 424/273 R
[58] Field of Search ............... 260/308 R; 548/341; 424/269, 273 R

[56] References Cited

U.S. PATENT DOCUMENTS

| | | | |
|---|---|---|---|
| 3,870,726 | 3/1975 | Jager et al. | 260/308 R |
| 4,086,351 | 4/1978 | Balasubramanyan et al. | 260/308 R |
| 4,104,399 | 8/1978 | Pommer et al. | 260/308 R |

Primary Examiner—Alton D. Rollins
Attorney, Agent, or Firm—Harry Falber

[57] ABSTRACT

Diphenylethene derivatives of the formula I given herein are new, very valuable microbicides. They can be used on their own or in the form of pesticidal compositions for combating or preventing attack by phytopathogenic fungi, such as mildew and scab diseases.

15 Claims, No Drawings

1,1-DIPHENYLETHENE DERIVATIVES AS MICROBICIDES

The present invention relates to 1.1-diphenylethene derivatives, to their production, and to their use for combating fungi, as well as to microbicidal compositions which contain such compounds as active ingredients.

The new compounds correspond to the formula I:

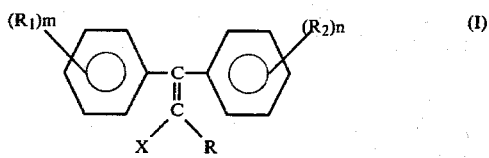

in which X is fluorine or chlorine; R is a 1,2,4-triazolyl-1 group or imidazolyl-1 group, each of which is unsubstituted or substituted by methyl; whilst $R_1$ and $R_2$ independently of one another are each a number, determined by m and n respectively, of identical or different substituents from the group; halogen, $C_1$-$C_3$-alkyl, $-CF_3$ or $-CN$; and m and n independently of one another are each 0, 1, 2 or 3.

Compounds of the formula I can be designated as 1.1-diphenyl-2-haloethenes and, depending on the heterocycle R, are accordingly 1.1-diphenyl-2-halo-2-(1,2,4-triazolyl-1)-ethenes and 1.1-diphenyl-2-halo-2-(imidazolyl-1)-ethenes. respectively.

The salts tolerant to plants of the compounds of the formula I with inorganic or organic acids, and also corresponding metal complex salts with Cu salts, Mn salts, Zn salts and Fe salts and other salts, are taken as being embraced by the formula I.

Compounds of the formula I are derived in the majority of cases structurally from the chemical group of DDT analogues, but have no insecticidal action and are readily decomposed under natural conditions.

It has now been found that, surprisingly, compounds having the structure of the formula I exhibit for practical requirements a very favourable microbicidal spectrum for the protection of cultivated plants, without disadvantageously influencing these as a result of undesirable secondary effects. Cultivated plants within the scope of the present invention are, for example: cereals, (wheat, barley, rye, oats and sorghum), maize, rice, vegetables, sugar beet, soya bean, groundnuts, fruit trees, ornamental plants, grape vines, hops, cucumber plants (cucumbers, pumpkins, melons), solanaceae, such as potatoes, tobacco and tomatoes, and also bananas, cocoa and natural rubber plants.

Fungi occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such fungi. The active substances are effective against the phytopathogenic fungi belonging to the following classes: Phycomycetes such as Oomycetes species, Basidiomycetes such as in particular rust fungi (for example Puccinia); Fungi imperfecti (for example Verticillium, Piricularia, Cercospora); especially however against the pathogens of varieties of mildew, belonging to the Ascomycetes class, such as Erysiphe and Podosphaera, as well as against Venturia and others. Furthermore, the compounds of the formula I have a systemic action. They can also be used as dressing agents for the treatment of seed (fruits, tubers and grain), and plant cuttings to protect them from fungus infections, and also against phytopathogenic fungi occurring in the soil.

Preferred compounds of the formula I as plant fungicides are those in which X is fluorine. This group is to be called subgroup Ia.

Further preferred compounds of the formula I are those in which the substituents $R_1$ and $R_2$ occupy one of the ortho- or para-positions of the phenyl rings. When they are derived from the subgroup Ia, such compounds are to be called subgroup Ib.

Particularly preferred compounds of the formula I are those in which R is the unsubstituted 1,2,4-triazolyl-1 -group, especially those compounds which are derived from the subgroup Ib, and which are to be called here subgroup Ic.

Active substances especially preferred in the subgroup Ic are those in which in at least two of the four positions 2,4 and 2',4' of both phenyl rings there are 2 halogen atoms from the group fluorine and chlorine, and in the six positions 3,5,6 and 3',5',6' there are hydrogen atoms. This particularly preferred subgroup is to be called Id.

Very highly effective plant fungicides are, inter alia, the following individual compounds:
(a) α,α-bis-(4-chlorophenyl)-β-fluoro-β-(1,2,4-triazolyl-1)-ethene,
(b) α,α-bis-(2-chlorophenyl)-β-fluoro-β-(1,2,4-triazolyl-1)-ethene,
(c) α-phenyl-α-(2,4-dichlorophenyl)-β-fluoro-β-(1,2,4-triazolyl-1)-ethene,
(d) α-(4-fluorophenyl)-α-(2,4-dichlorophenyl)-β-fluoro-β-(1,2,4-triazolyl-1)-ethene,
(e) α,α-bis-(4-fluorophenyl)-β-fluoro-β-(1,2,4-triazolyl-1)-ethene,
(f) α-(4-chlorophenyl)-α-(2,4-dichlorophenyl)-β-fluoro-β-(1,2,4-triazolyl-1)-ethene,
(g) α,α-bis-(2,4-dichlorophenyl)-β-fluoro-β-(1,2,4-triazolyl-1)-ethene, and
(h) α,α-bis-(2-chloro-4-fluorophenyl)-β-fluoro-β-(1,2,4-triazolyl-1)-ethene.

These compounds display a particularly strong action in combating varieties of mildew. Applied in the customary amounts for fungicide application, compounds of the formula I are tolerant to plants, and furthermore produce no change in plant growth.

Compounds of the formula I are produced in the first place in the same manner as, or in a similar manner to, DDT and analogues thereof (see for example German Patent Specification No. 547,871).

One of the possible known methods for producing symmetrical diphenylethene derivatives comprises condensation of the appropriately substituted benzene derivative with fluoral (or chloral) to give a DDT analogue, from which is split off, with a base, one mol of HX to form a DDE analogue II:

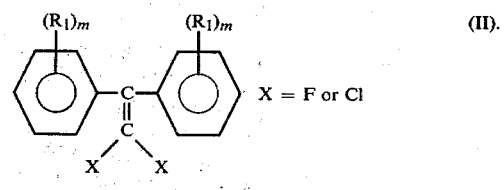

To produce unsymmetrical intermediates of the formula III

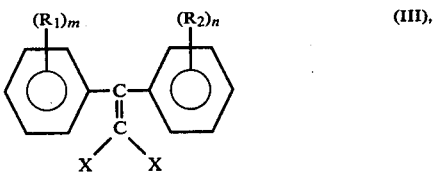

in which $R_1$ and $R_2$ or m and n are not the same, the procedure followed is analogous and molar amounts of fluoral (or chloral) are condensed to give an intermediate IV, which is condensed with a further benzene derivative, and subsequently one mol of HX is split off:

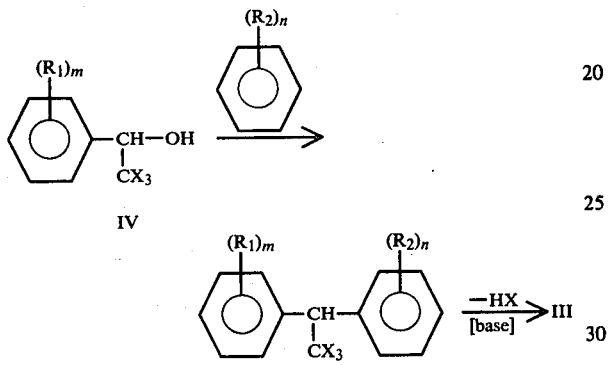

In order to obtain compounds of the formula I, it is possible by using equimolar amounts of the intermediates II or III to exchange one of the two halogen atoms on the double bond for the heterocycle R, with 1 mol of HX being simultaneously split off. The reaction can also be frequently simplified by performing the splitting-off of HX, to give the intermediates II or III, already in the presence of the heterocycle R, so that II or III react in statu nascendi with 1,2,4-triazole or imidazole.

Intermediates of the formula IV can as is known be obtained also by a Grignard reaction of a benzene derivative appropriately substituted with $R_1$ (or $R_2$), and further reaction of the formed phenyl magnesium bromide derivative with
  fluoral or chloral, or
  trifluoroacetic acid or trichloroacetic acid, preferably in the form of their respective alkali metal salts, and subsequent catalytic hydrogenation ($H_2$/Pd) of the resulting trihaloacetophenone V

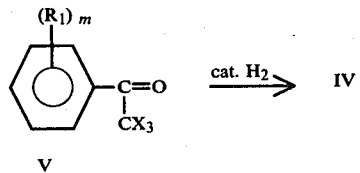

The product V can be hydrogenated, instead of catalytically, also with $NaBH_4$ or $LiAlH_4$ to the carbinol IV.

There are a number of other processes for producing the, for the most part, known α,α-diphenylethane derivatives or α,α-diphenylethene derivatives, which can be used as intermediates in the processes of the present invention.

The invention relates to a process for producing compounds of the formula I by reaction of an α,α-diphenyl-β,β-dihaloethene of the formula III with unsubstituted or methyl-substituted imidazole or 1,2,4-triazole.

To produce compounds of the formula I in which X is chlorine, higher temperatures up to 200° C. are required, in some cases the reaction has to be performed under pressure. Compounds in which X is fluorine can be obtained under milder conditions, for example from room temperature up to a maximum of 100° C.

Inert solvents where necessary are used. Polar solvents such as glyme (ethylene glycol dimethyl ether), dimethyl sulfoxide, dimethylformamide, dioxane, water, and so forth, are preferred. The addition of an inorganic base or of a tertiary amine, besides the basic reactants, is advisable.

With varying substituted phenyl rings, there is obtained a mixture of cis/trans isomers of the formula I. The pure antipodes have a dissimilar microbicidal action.

The production of compounds of the formula I is illustrated in the following Examples. Temperature values throughout are in degrees Centigrade.

EXAMPLE 1

Production of

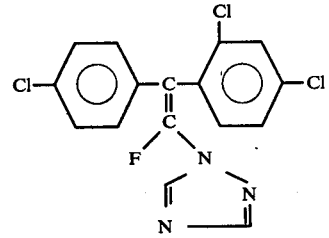

α-(4-Chlorophenyl)-α-(2,4-dichlorophenyl)-β-fluoro-β-(1,2,4-triazolyl-1)-ethene [compound 16]

1 mol (339.5 g) of α-(p-chlorophenyl)-α-(o,p-dichlorophenyl)-β,β,β-trifluoroethane is placed into 1 liter of "glyme" (=ethylene glycol dimethyl ether), and 82 g of triazole (=25% excess) is added to the solution. There is then added dropwise at 80°-85°, within one hour, 250 ml of 60% KOH solution. The reaction mixture is then held at 80° for 4 hours. After cooling, the two phases are separated, and the organic phase is dried in the customary manner with Na sulfate, and concentrated by evaporation to yield a light-coloured oil (320 g), which can be distilled in vacuo (b.p.: 180°-185°/0.2 Torr). It is a mixture of the two possible cis-trans isomers. By using ether and cyclohexane, a part of the oil can be caused to crystallise. The crystallised product is one of the two isomers (m.p.=94°-95°).

EXAMPLE 2

Production of

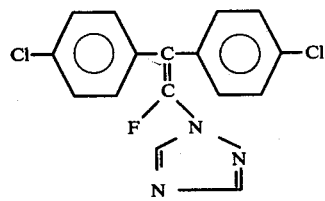

α,α-Bis-(4-chlorophenyl)-β-fluoro-β-(1,2,4-triazolyl-1)-ethene [compound 3]

The reaction is performed in a manner analogous to that described in Example 1. Since in the case of this compound no geometrical isomers are possible, the product is obtained immediately in the crystalline form after the organic phase has been evaporated. Recrystallisation from cyclohexane and ether yields the analytically pure compound, m.p. 105°–106°.

EXAMPLE 3

Production of

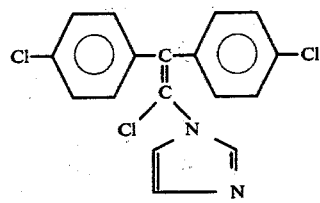

α,α-Bis-(4-chlorophenyl)-β-chloro-β-(imidazolyl-1)-ethene 1 mol (318 g) of "DDE" [=2,2-bis-(p-chlorophenyl)-1,1-dichloroethene] is heated, without solvent, with 3 mols of imidazole (204 g) for 20 hours at 200°–210° in a pressure tube. About 1.5 liters of water are then added to the reaction mixture, and the whole is taken up in ether. On being concentrated by evaporation, the ether solution leaves behind a viscous oil. This can be freed from dark, difficultly volatile constituents by high-vacuum distillation (b.p. 170°–180°/0.005 Torr). The compound can be obtained pure by recrystallisation from cyclohexane. It has a melting point of 104°–105°.

EXAMPLE 4

Production of

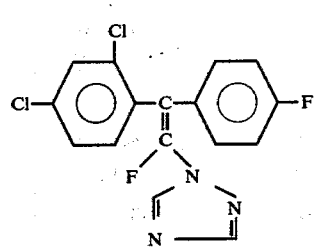

α-(4-Fluorophenyl)-α-(2,4-dichlorophenyl)-β-fluoro-β-(1,2,4-triazolyl-1)-ethene [compound 23]

(a) A spatula tip of iodine is added to 24 g of Mg in 200 ml of diethyl ether, and 175 g (1 mol) of p-fluorochlorobenzene in 800 ml of diethyl ether is added dropwise in such a manner that the exothermically reacting mixture boils under reflux. After 2 hours, the reaction mixture is cooled to 0°–10°, and 152 g (1 mol) of anhydrous $CF_3$—COO—K is added. The dispersion obtained is stirred overnight at room temperature; it is then cooled and 250 ml of 20% hydrochloric acid is added. The ethereal phase is separated, washed neutral with water and concentrated by evaporation. Vacuum distillation of the residue yields 91 g (about 50%) of p-fluorotrifluoroacetophenone, b.p. 50°–52°/20 mbars.

(b) 212 g (1 mol) of p-fluorotrifluoroacetophenone is dissolved in 1000 ml of ethanol; to the solution at 0°–10° is added 20 g of $NaBH_4$, and the whole is stirred for 2 hours, and then for a further 4 hours at room temperature. 500 ml of water is slowly added, and the supernatant clear solution is decanted, and subsequently concentrated in a rotary evaporator. The residue is dissolved in diethyl ether, the solution is washed with water, dried with sodium sulfate and concentrated by evaporation. The oily residue is fractionally distilled to yield 171 g of p-fluorophenyl-trifluoromethyl carbinol, b.p. 86°–90° C./20 mbars.

(c) 300 ml of 1,3-dichlorobenzene is placed into 1000 ml of concentrated sulfuric acid, and at 0°–10° C. is added dropwise 214 g (1 mol) of the carbinol obtained under (b). The reaction mixture is stirred overnight at room temperature; it is poured onto ice, and 300 ml of methylene chloride is added. The organic phase is washed neutral with water, dried over sodium sulfate and concentrated by evaporation to obtain 260 g of α-(4-fluorophenyl)-α-(2,4-dichlorophenyl)-β,β,β-trifluoroethane, b.p. 95°–105°/0.13 mbar.

(d) 90.4 g (0.28 mol) of the intermediate obtained under (c) in 300 ml of "glyme" with 21.3 g (0.31 mol) of 1,2,4-triazole is heated at 80° C. (reflux). A solution of 47 g of KOH in 100 ml of water is added dropwise in the course of 1 hour. The reaction mixture is then refluxed for 6 hours. After cooling, the organic phase is washed with a saturated sodium chloride solution and concentrated by evaporation. The viscous residue is distilled under high vacuum: b.p. 200°/0.015 mbar. Recrystallisation from hexane yields the pure product, b.p. 70°–72°.

EXAMPLE 5

Production of

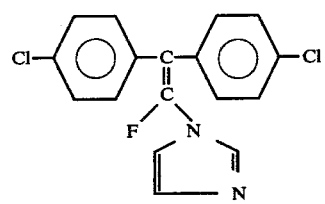

α,α-Bis-(4-chlorophenyl)-β-fluoro-β-(imidazolyl-1)-ethene [compound 52]

1 mol (285 g) of 2,2-bis-(p-chlorophenyl)-1,1-difluoroethylene is dissolved in 2 liters of dimethylformamide. There is then added to the solution at 0°–5° 56 g of finely pulverised KOH, and at 0°–5° dropwise, in the course of two hours, 67 g of imidazole dissolved in 500 ml of dimethylformamide.

The reaction mixture is held for a further 3 hours at 0°–5°, and is subsequently allowed to stand at 20° for 12 hours. Three liters of water are then added, and extraction is performed with ether. The ether is evaporated off to leave 210 g of the final product as a solid residue, which can be recrystallised from ethanol; m.p. 90°–91°.

EXAMPLE 6

Production of

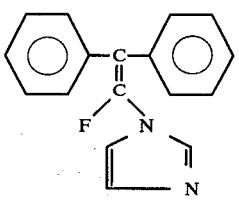

α,α-Diphenyl-β-fluoro-β-(imidazolyl-1)-ethene [compound 50]

1 mol (236 g) of trifluorodiphenylethane is dissolved in 1 liter of "diglyme" [bis-(methoxyethyl)-ether], and to this solution are added 75 g of imidazole, dissolved in 250 ml of water, and 125 g of KOH, dissolved in 250 ml of water. The mixture is heated with stirring for 8 hours at 100°–110°. In further processing, the major amount of solvent is evaporated off in vacuo; 1 liter of water is then added to the residue, and extraction is performed with methylene chloride. The methylene chloride solution is dried with sodium sulfate and concentrated by evaporation. The residue is distilled at 0.5 Torr, and as first runnings is obtained about 30 g of starting material. The main amount (about 200 g) distills between 140° and 150°/0.5 Torr. On stirring with hexane and an amount of ether, the substance is obtained in crystalline form. The yield after drying in vacuo is 180 g of final product, m.p. 48°–50°.

EXAMPLE 7

Production of

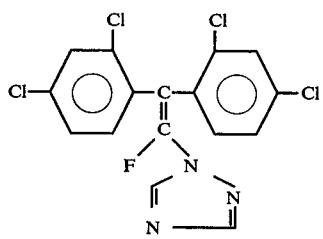

α,α-Bis-(2,4-dichlorophenyl)-β-fluoro-β-(1,2,4-triazolyl-1)-ethene [compound 4]

1 mol (374 g) of α,α-bis-(2,4-dichlorophenyl)-β,β,β-trifluoroethane (obtained by condensation of m-dichlorobenzene with fluoral in the presence of concentrated sulfuric acid) is dissolved in 800 ml of "glyme". There is then added with stirring 80 g of 1,2,4-triazole, and at 80°–85° there is subsequently added dropwise 250 ml of 60% KOH. The reaction mixture is refluxed for about a further 3 hours. After cooling, the aqueous phase is separated and discarded. The organic phase is concentrated by evaporation, and the residue is subjected to molecular distillation under high vacuum. The substance distills over at 180° and 0.1 Torr as colourless oil, which solidifes on cooling to form a solid resin. The yield is about 76%. The compound can be crystallised from a mixture of cyclohexane and methanol: m.p. 84°–86°.

In this manner or by one of the above-given methods are produced the following compounds of the formula:

| Comp. No. | X | $R_3$ | $R_4$ | $R_5$ | $R_6$ | Physical constants |
|---|---|---|---|---|---|---|
| 1 | F | H | H | H | H | m.p. 78°–79° |
| 2 | F | 2-Cl | H | 2-Cl | H | m.p. 80°–82° |
| 3 | F | H | Cl | H | Cl | m.p. 105°–106° |
| 4 | F | 2-Cl | Cl | 2-Cl | Cl | m.p. 84°–86° |
| 5 | F | 3-Cl | Cl | 3-Cl | Cl | |
| 6 | F | 2-$CH_3$ | Cl | 2-$CH_3$ | Cl | |
| 7 | F | H | $CH_3$ | H | $CH_3$ | b.p. 175° / 0.13mbar |
| 8 | F | 3-$CH_3$ | Cl | 3-$CH_3$ | Cl | |
| 9 | F | 3-$CF_3$ | H | 3-$CF_3$ | H | |
| 10 | F | 3-$CF_3$ | Cl | 3-$CF_3$ | Cl | |
| 11 | F | H | F | H | F | m.p. 93°–94° |
| 12 | F | H | Br | H | Br | |
| 13 | F | H | CN | H | CN | viscous oil |
| 14 | F | 2-Cl | CN | 2-Cl | CN | |
| 15 | F | 2-$CH_3$ | CN | 2-$CH_3$ | CN | |
| 16 | F | H | Cl | 2-Cl | Cl | m.p. 94°–95° |
| 17 | F | 2-Cl | H | H | Cl | m.p. 98°–100° |
| 18 | F | H | Cl | 2-$CH_3$ | $CH_3$ | b.p. 200° / 0.13mbar |
| 19 | F | H | Cl | 3-$CH_3$ | $CH_3$ | m.p. 121°–125° |
| 20 | F | H | Cl | H | H | b.p. 170° / 0.13mbar |
| 21 | F | H | H | 2-Cl | Cl | m.p. 88°–89° |
| 22 | F | H | $CH_3$ | 2-Cl | Cl | m.p. 143°–144° |
| 23 | F | H | F | 2-Cl | Cl | m.p. 70°–72° |
| 24 | F | H | isoC$_3$H$_7$ | 2-Cl | Cl | |
| 25 | F | 2-$C_2H_5$ | Cl | 2-$C_2H_5$ | Cl | |
| 26 | Cl | 2-Cl | H | 2-Cl | H | m.p. 88°–91° |
| 27 | Cl | H | Cl | H | Cl | m.p. 111°–113° |
| 28 | Cl | 2-Cl | Cl | 2-Cl | Cl | b.p. 185° / 0.13mbar |
| 29 | Cl | 3-Cl | Cl | 3-Cl | Cl | |
| 30 | Cl | 2-$CH_3$ | Cl | 2-$CH_3$ | Cl | |
| 31 | Cl | 3-$CH_3$ | Cl | 3-$CH_3$ | Cl | |
| 32 | Cl | 3-$CF_3$ | H | 3-$CF_3$ | H | oil |
| 33 | Cl | 3-$CF_3$ | Cl | 3-$CF_3$ | Cl | oil |
| 34 | Cl | H | Br | H | Br | resin |
| 35 | Cl | H | Cl | 2-Cl | Cl | |
| 36 | Cl | 2-Cl | H | H | Cl | |
| 37 | Cl | H | H | 2-Cl | Cl | oil |
| 38 | Cl | 2-$C_2H_5$ | Cl | 2-$C_2H_5$ | Cl | oil |
| 39 | F | 2-Cl | F | 2-Cl | F | m.p. 82°–85° |
| 40 | F | H | $CF_3$ | H | F | oil |
| 41 | F | 2-Cl | F | H | F | m.p. 190°–197° C./ 0.5mbar |
| 42 | F | 2-$CF_3$ | Cl | H | F | viscous |
| 43 | F | H | Cl | H | $CF_3$ | m.p. 99°–102° |
| 44 | F | 2-Cl | Cl | H | $CF_3$ | b.p. 161°–163° C./ 0.66mbar |
| 45 | F | 2-Cl | Cl | H | CN | b.p. 157°–160°/ 0.66mbar |
| 46 | F | 2-F | Cl | 2-F | Cl | m.p. 90°–93° |
| 47 | F | H | Cl | H | F | m.p. 73°–77° |
| 48 | F | 2-Cl | Cl | 2-Cl | F | m.p. 61°–64° |
| 49 | F | 2-Cl | Cl | 2-F | F | viscous |

In an analogous manner are produced also the compounds of the formula

[Structure: diphenyl compound with R3, R4 on left ring, R5, R6 on right ring, C=C with F and N-triazole]

| Comp. No. | R₃ | R₄ | R₅ | R₆ | Physical constants |
|---|---|---|---|---|---|
| 50 | H | H | H | H | m.p. 48°–50° |
| 51 | 2-Cl | H | 2-Cl | H | m.p. 65°–66° |
| 52 | H | Cl | H | Cl | m.p. 90°–91° |
| 53 | 2-Cl | Cl | 2-Cl | Cl | m.p. 78°–80° |
| 54 | 3-Cl | Cl | 3-Cl | Cl | m.p. 105°–107° |
| 55 | 2-CH₃ | Cl | 2-CH₃ | Cl | |
| 56 | H | CH₃ | H | H | b.p. 145°–148°/ 0.13mbar |
| 57 | 3-CH₃ | Cl | 3-CH₃ | Cl | |
| 58 | 3-CF₃ | H | 3-CF₃ | H | |
| 59 | 3-CF₃ | Cl | 3-CF₃ | Cl | |
| 60 | H | F | H | F | |
| 61 | H | Br | H | Br | m.p. 98°–104° |
| 62 | H | CN | H | CN | |
| 63 | 2-Cl | CN | 2-Cl | CN | resin |
| 64 | 2-CH₃ | CN | 2-CH₃ | CN | |
| 65 | H | Cl | 2-Cl | Cl | |
| 66 | 2-Cl | H | H | Cl | m.p. 84°–85° |
| 67 | H | Cl | 2-CH₃ | CH₃ | |
| 68 | H | Cl | 3-CH₃ | CH₃ | |
| 69 | H | Cl | H | H | m.p. 67°–69° |
| 70 | H | H | 2-Cl | Cl | |
| 71 | H | CH₃ | 2-Cl | Cl | |
| 72 | 2-CH₃ | H | H | H | b.p. 140°–150°/ 0.25mbar |
| 73 | H | C₂H₅ | H | C₂H₅ | oil |

By one of the above-given methods are produced also the following polysubstituted compounds of the formula

[Structure: diphenyl compound with Cl at position 4 on left ring, R3, R7 on left ring, R5, R6, R8 on right ring, C=C with F and N-triazole]

| Comp. No. | R₃ | R₇ | R₅ | R₆ | R₈ | Physical constants |
|---|---|---|---|---|---|---|
| 74 | 2-Cl | 6-CH₃ | 2-Cl | 4-Cl | 6-CH₃ | resin |
| 75 | 2-Cl | 6-Cl | 2-Cl | 4-Cl | 6-Cl | |
| 76 | 2-F | 6-F | 2-F | 4-Cl | 6-F | oil |
| 77 | 2-CH₃ | 6-CH₃ | 2-CH₃ | 4-Cl | 6-CH₃ | oil |
| 78 | 2-CN | 6-Cl | 2-CN | 4-Cl | 6-Cl | |
| 79 | 2-Cl | 6-C₂H₅ | 2-Cl | 4-Cl | 6-C₂H₅ | |
| 80 | 2-Cl | H | 2-CH₃ | 4-CH₃ | 6-CH₃ | viscous |
| 81 | H | H | 2-CH₃ | 4-CH₃ | 6-CH₃ | |
| 82 | H | H | 2-Cl | 4-Cl | 5-Cl | b.p. 240° C./ 0.55mbar | and also the compounds

No. 83 [Structure with 2-Cl, 4-Cl substituents, C=C-F, N-triazole with CH₃] m.p. 87°–90°

No. 84 [Structure with 2-Cl, 4-Cl on both rings, C=C-F, N-triazole with CH₃] b.p.150°–160°/ 0.66mbar The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

solid preparations:
  dusts and scattering agents (up to 10%), granulates [coated granules, impregnated granules and homogeneous granules] or pellets (1 to 80%);

liquid preparations:
  (a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);
  (b) solutions (0.1 to 20%); aerosols The active substances of the formula I of the present invention can be formulated for example as follows:

Dust:
The following substances are used to produce (a) a 5% dust and (b) a 2% dust:

(a)
5 parts of active substance, and
95 parts of talcum;

(b)
2 parts of active substance,
1 part of highly dispersed silicic acid, and
97 parts of talcum.

The active substances are mixed and ground with the carriers, and in this form they can be applied by dusting.

Granulate:
The following substances are used to produce a 5% granulate:
5 parts of active substance,
0.25 part of epichlorohydrin,
0.25 part of cetyl polyglycol ether, 3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin, and the acetone is evaporated off in vacuo. A microgranulate of this type is advantageously used for combating soil fungi.

Wettable powder:

The following constituents are used to produce (a) a 70% wettable powder, (b) a 40% wettable powder, (c) and (d) a 25% wettable powder, and (e) a 10% wettable powder:

(a)

70 parts of active substance,
5 parts of sodium dibutylnaphthylsulfonate,
3 parts of naphthalenesulfonic acid/phenolsulfonic acid/formaldehyde condensate 3:2:1,
10 parts of kaolin, and
12 parts of Champagne chalk;

(b)

40 parts of active substance,
5 parts of sodium lignin sulfonate,
1 parts of sodium dibutylnaphthalenesulfonate, and
54 parts of silicic acid;

(c)

25 parts of active substance,
4.5 parts of calcium lignin sulfonate,
1.9 parts of Champagne chalk/hydroxyethyl cellulose mixture (1:1).
1.5 parts of sodium dibutylnaphthalenesulfonate,
19.5 parts of silicic acid,
19.5 parts of Champagne chalk, and
28.1 parts of kaolin;

(d)

25 parts of active substance,
2.5 parts of isooctylphenoxy-polyoxyethylene ethanol,
1.7 parts of Champagne chalk/hydroxyethylcellulose mixture (1:1),
8.3 parts of sodium aluminium silicate,
16.5 parts of kieselgur, and
46 parts of kaolin; and (e)

10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, and which can be diluted with water to give suspensions of the desired concentration, and these are particularly suitable for leaf application.

Emulsifiable concentrate:

The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the desired concentration can be prepared from these concentrates by dilution with water, and they are particularly suitable for leaf application.

The concentrations of active substance in the following biological Examples are given in ppm (100 ppm=0.01%).

EXAMPLE 8

Action against Cercospora personate (=C. arachidicola) on groundnut plants

Three-week old groundnut plants are sprayed with a spray liquor produced from wettable powder of the active substance (200 ppm of active substance). The treated plants are dusted after about 12 hours with a conidiospore suspension of the fungus. The infected plants are then incubated for about 24 hours at >90% relative humidity, and are subsequently transferred to a greenhouse at about 22°. The fungus infection is assessed after 12 days.

In comparison with the untreated control plants, plants which have been treated with active substances of the formula I display only slight fungus infection or no fungus infection. The compounds Nos. 18, 21, 23, 39 and 41 even at a concentration of 60 ppm completely prevent fungus infection.

EXAMPLE 9

Action against Erysiphe graminis on barley plants

Residual protective action

Barley plants about 8 cm in height are sprayed with a spray liquor prepared from wettable powder of the active substance (20 ppm of active substance). The treated plants are dusted after 48 hours with conidia of the fungus. The infected barley plants are placed into a greenhouse at about 22°, and the fungus infestation is assessed after 10 days.

The compounds of the formula I are as a rule highly effective against barley mildew. The mildew infection is completely prevented with the compounds Nos. 1, 2, 3, 4, 7, 11, 16, 17, 18, 20, 21, 22, 23, 39, 41 and 82.

EXAMPLE 10

Action against Podosphaera leucotricha on apple-tree cuttings

Residual-protective action

Apple-tree cuttings having new shoots about 15 cm long are sprayed with a spray liquor prepared from wettable powder of the active substance (200 ppm of active substance). The treated plants are infected after 24 hours with a conidiospore suspension of the fungus, and are kept in a climatic chamber at 70% relative humidity at 20°. The assessment of the fungus infection is made 12 days after infection. The fungus infection is prevented completely with the active substances Nos. 2, 4, 16, 18, 21, 23, 39 and 41.

EXAMPLE 11

Action against Venturia inaequalis on apple-tree cuttings

Residual-protective action

Apple-tree cuttings having new shoots 10–20 cm long are sprayed with a spray liquor prepared from wettable powder of the active substance (200 ppm of active substance). The treated plants are infected after 24 hours with a conidiospore suspension of the fungus. The plants are then incubated during 5 days with 90–100% relative humidity, and for a further 10 days they are kept in a greenhouse at 20°–24°. Scab infection is completely prevented with the active substances Nos. 21, 23, 39 and 41.

EXAMPLE 12

Action against seed-borne fungi on cereals

Action against Helminthosporium gramineum

Wheat seeds are contaminated with a spore suspension of the fungus, and again dried. The contaminated seeds are dressed with a suspension produced from wettable powder of the test substance (600 ppm of active substance relative to the weight of the seeds). After two days the seeds are laid out on suitable agar dishes, and after a further four days an assessment is made of the development of the fungus colonies around the seeds. Number and size of the pilz colonies are taken as a basis for evaluation of the test products. The fungus growth is completely inhibited with the compounds Nos. 11, 16, 21, 23 and 39.

EXAMPLE 13

Action against Puccinia graminis f. sp. secalis on rye

Residual-protective action

Rye plants are sprayed, 4 days after sowing, with a spray liquor prepared from wettable powder of the active substance (200 ppm of active substance). The treated plants are infected after 24 hours with an uredo spore suspension of the fungus. After an incubation time of 48 hours at 95–100% relative humidity at about 20°, the infected plants are placed into a greenhouse at about 22°. An assessment of the development of rust pustules is made 12 days after infection. Compared with the untreated but infected control plants, the plants infected but treated with the compounds of the formula I displayed a considerable reduction or complete absence of rust fungus. Plants which have been treated with active substances Nos. 11, 21, 23, 39 or 41 exhibit no infection.

By virtue of their broad fungus spectrum, compounds of the subgroup Id mentioned in the introduction, such as the active substances Nos. 21, 23 and 39, are to be particularly emphasised.

In order to broaden their spectrum of action, compounds of the formula I can be combined with known fungicides and bactericides, and also with herbicides, insecticides, acaricides, nematocides, plant-growth regulators or fertilisers.

What is claimed is:

1. A compound of the formula I

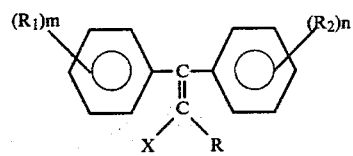

in which X is fluorine or chlorine; R is a 1,2,4-triazolyl-1 group or imidazolyl-1 group, each of which is unsubstituted or substituted by methyl; whilst $R_1$ and $R_2$ independently of one another are each a number, determined by m and n respectively, of identical or different substituents from the group: halogen, $C_1$–$C_3$-alkyl, $CF_3$ or —CN; and m and n independently of one another are each 0, 1, 2 or 3.

2. A compound of the formula I according to claim 1, wherein X is fluorine.

3. A compound of the formula I according to claim 2, wherein the substituents $R_1$ and $R_2$ occupy one of the ortho- or para-positions of the phenyl rings.

4. A compound of the formula I according to claim 2, wherein R is a 1,2,4-triazolyl-1 group.

5. A compound of the formula I according to claim 3, wherein R is a 1,2,4-triazolyl-1 group.

6. A compound of the formula I according to claim 5, wherein in at least two of the four positions 2,4 and 2',4' of both phenyl rings there are 2 halogen atoms from the group fluorine and chlorine, whilst in the remaining six positions 3,5,6 and 3',5',6' there are hydrogen atoms.

7. A compound according to claim 6 selected from
α-Phenyl-α-(2,4-dichlorophenyl)-β-fluoro-β-(1,2,4-triazolyl-1)-ethene;
α-(4-Fluorophenyl)-α-(2,4-dichlorophenyl)-α-fluoro-(1,2,4-triazolyl-1)-ethene and
α,α-Bis-(2-chloro-4-fluorophenyl)-β-fluoro-β-(1,2,4-triazolyl-1)-ethene.

8. A microbicidal composition containing as active substance a microbicidally effective amount of a compound of the formula I according to claim 1, together with suitable carriers and/or surface-active additives.

9. A composition according to claim 8 containing a compound of the formula I according to claim 2.

10. A composition according to claim 8 containing a compound of the formula I according to claim 3.

11. A composition according to claim 8 containing a compound of the formula I according to claim 4.

12. A composition according to claim 8 containing a compound of the formula I according to claim 5.

13. A composition according to claim 8 containing a compound of the formula I according to claim 6.

14. A composition according to claim 8 containing a compound selected from α-phenyl-α-(2,4-dichlorophenyl)-β-fluoro-β-(1,2,4-triazolyl-1)-ethene;
α-(4-fluorophenyl)-α-(2,4-dichlorophenyl)-β-fluoro-(1,2,4-triazolyl-1)-ethene and
α,α-bis-(2-chloro-4-fluorophenyl)-β-fluoro-β-(1,2,4-triazolyl-1)-ethene.

15. A method of combating phytopathogenic fungi and of preventing fungus infection which comprises applying to the locus to be protected a fungicidally effective amount of a compound according to claim 1.